United States Patent
Hale et al.

(10) Patent No.: US 7,811,224 B2
(45) Date of Patent: Oct. 12, 2010

(54) METHOD FOR DEALING WITH SINGULARITIES IN GRAVITY REFERENCED ENDOSCOPIC IMAGING

(75) Inventors: Eric Lawrence Hale, Altadena, CA (US); Hans David Hoeg, Arcadia, CA (US); Nathan Jon Schara, Pasadena, CA (US)

(73) Assignee: Karl Storz Development Corp., Goleta, CA (US)

( * ) Notice: Subject to any disclaimer, the term of this patent is extended or adjusted under 35 U.S.C. 154(b) by 1369 days.

(21) Appl. No.: 11/055,445

(22) Filed: Feb. 10, 2005

(65) Prior Publication Data

US 2006/0100482 A1  May 11, 2006

Related U.S. Application Data

(60) Provisional application No. 60/626,122, filed on Nov. 9, 2004.

(51) Int. Cl.
*A61B 1/00* (2006.01)
(52) U.S. Cl. ..................................... 600/103
(58) Field of Classification Search ................ 600/101, 600/103, 109, 117, 118, 173
See application file for complete search history.

(56) References Cited

U.S. PATENT DOCUMENTS

| | | | | |
|---|---|---|---|---|
| 4,902,129 | A * | 2/1990 | Siegmund et al. | 356/241.4 |
| 5,899,851 | A * | 5/1999 | Koninckx | 600/117 |
| 6,434,507 | B1 * | 8/2002 | Clayton et al. | 702/152 |
| 7,122,001 | B2 * | 10/2006 | Uchiyama et al. | 600/103 |
| 7,211,042 | B2 * | 5/2007 | Chatenever et al. | 600/117 |
| 2002/0161280 | A1 * | 10/2002 | Chatenever et al. | 600/112 |
| 2003/0220541 | A1 | 11/2003 | Salisbury, Jr. et al. | 600/101 |
| 2004/0127769 | A1 | 7/2004 | Hale et al. | 600/173 |
| 2004/0210105 | A1 | 10/2004 | Hale et al. | 600/101 |
| 2005/0020878 | A1 * | 1/2005 | Ohnishi et al. | 600/117 |

FOREIGN PATENT DOCUMENTS

| EP | 1 466 552 | 10/2004 |
|---|---|---|
| JP | 6269403 A | 9/1994 |

OTHER PUBLICATIONS

European Search Report; Feb. 16, 2006; 5 pages.

* cited by examiner

*Primary Examiner*—Philip R Smith
(74) *Attorney, Agent, or Firm*—St. Onge Steward Johnston & Reens LLC

(57) ABSTRACT

A method for avoiding rapid or sudden image rotation or reversal in a gravity leveled endoscopic imaging system is disclosed. A mathematical neighborhood of a singular viewing configuration is defined and within this neighborhood the endoscopic image orientation follows specified rules.

16 Claims, 11 Drawing Sheets

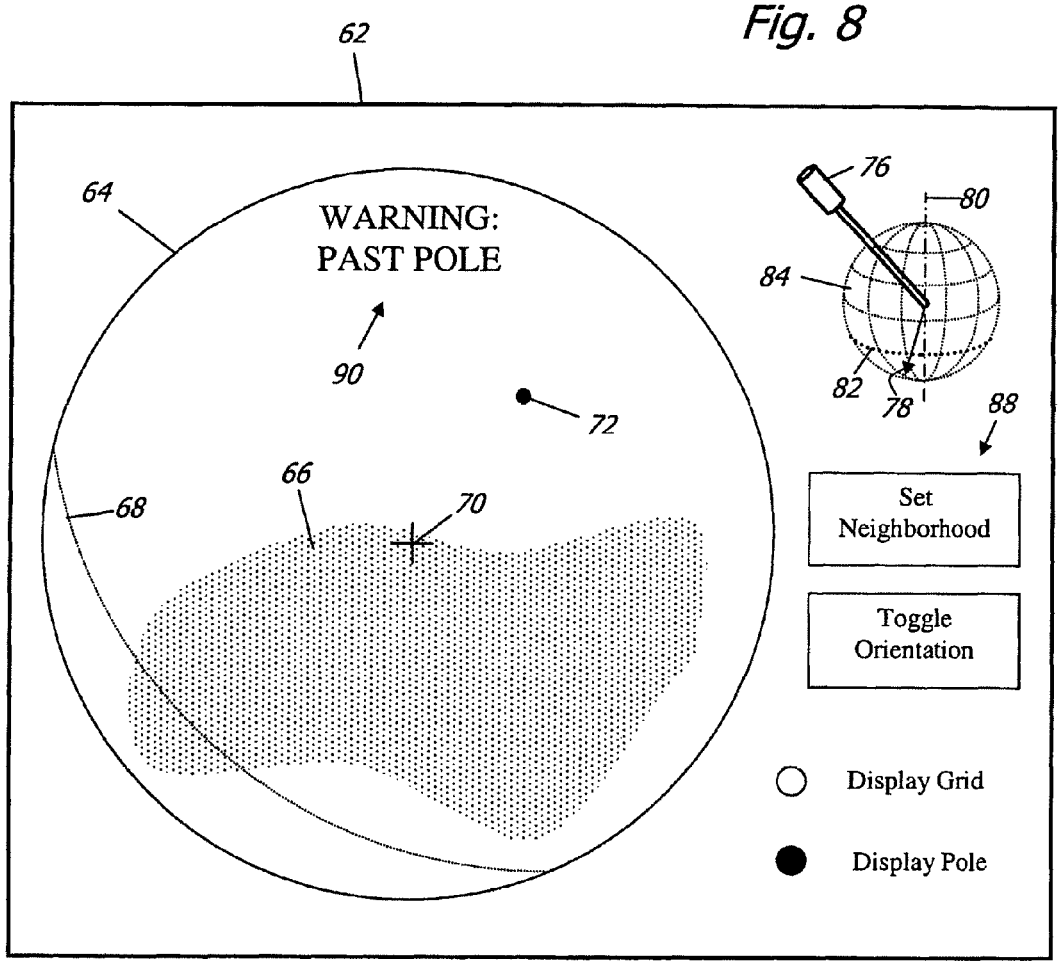

METHOD FOR DEALING WITH SINGULARITIES IN GRAVITY REFERENCED ENDOSCOPIC IMAGING

CROSS-REFERENCE TO RELATED APPLICATIONS

This application claims the benefit of U.S. provisional application Ser. No. 60/626,122 filed on Nov. 9, 2004, entitled "Method for Dealing with Singularities in Gravity Referenced Endoscopic Imaging", the contents of which are incorporated herein by reference.

STATEMENT REGARDING FEDERALLY SPONSORED RESEARCH

Not Applicable

FIELD OF THE INVENTION

The present invention relates to endoscopic imaging, and in particular to endoscopic image orientation and its relationship to the direction of gravity and the viewer's reference frame.

BACKGROUND OF THE INVENTION

As a surgeon or an assistant manipulates an endoscope with an attached camera, the camera faithfully relates what it sees, with its own upright axis displayed as the upright axis of the image on the display. This often results in rotation of the viewed image. As the image rotates, the surgeon loses track of what is actually up and down inside the endoscopic cavity. This disorientation is one of endoscopy's greatest enemies and has lead to severe mistakes such as the snipping of optical nerves which during a procedure were believed to be a different part of the anatomy. In open procedures, the surgeon can see the anatomy directly and therefore does not have a disorientation problem. However, during an endoscopic procedure the surgeon's viewpoint is different from the viewpoint of the endoscope, and the surgeon must continuously try to correlate his own mental picture of the anatomy with the endoscopic picture on the display. In doing this, the need to know what is up and down inside the endoscopic cavity is so strong that it has become common for surgeons to observe the flow direction of fluid droplets on the endoscope cover window or search for pooling blood in order to get a sense of direction inside the cavity. Aside from being important for distinguishing anatomical features which may look similar, knowing the up direction helps in understanding the endoscope's position relative to the surrounding anatomy. Ideally, the surgeon would be able to relate to the endoscopic cavity as if his own eyes were actually inside the cavity.

Attempted solutions to this problem have been proposed in U.S. Pat. No. 5,307,804 to Bonnet (1994), U.S. Pat. No. 5,899,851 to Koninckx (1999), U.S. Pat. No. 6,097,423 to Mattsson-Boze, et al. (2000), U.S. Pat. No. 6,471,637 to Green, et al. (2002), U.S. patent application Ser. No. 10/093,650 by Chatenever, et al. (2002), and U.S. patent application Ser. Nos. 10/829,767 and 60/560,172 by Schara et al. (2004), which are incorporated herein by reference in their entireties. The objects of these inventions are to provide schemes which can maintain the proper upright gravity-leveled orientation of the endoscopic image regardless of how the endoscope is being manipulated.

None of these solutions address the problem of so-called viewing singularities (poles). In a singular viewing configuration there is no unique upright image orientation. This occurs when the viewing direction (described as a view vector) is parallel to the direction of gravity. Although a mathematical discontinuity exists only at a singularity itself, the effect of the singularity is nearly everywhere and decreases as one moves away from it.

A viewing singularity is similar to standing on the North Pole and having to define which direction is south. In gravity-leveled endoscopic systems singularities cause the endoscopic image to suddenly flip or spin rapidly. This is obviously confusing and annoying to the user. Until now, it has not been clear how one should deal with situations where there is no defined up or down in the endoscopic image.

Thus, it is an object of this invention to provide a method for dealing with singularities in gravity-leveled endoscopic imaging systems such that the endoscopic image does not unexpectedly flip or spin during the endoscopic viewing process. It is an additional object of this invention to be applicable to any axial, oblique, side, or retro viewing endoscope as well as any endoscope with a variable direction of view.

BRIEF SUMMARY OF THE INVENTION

In a gravity leveled endoscopic imaging system, when the user moves the view vector towards a singular configuration, a warning flag is shown. The current image orientation is also maintained when the view vector is in the neighborhood of a singular configuration, thus avoiding sudden flipping or spinning of the image. Also, an option for the user to interactively control the flip or spin of the image when in such a neighborhood is provided. What is claimed is a method for avoiding rapid or sudden image rotation in a gravity leveled endoscopic imaging system, comprising monitoring of the attitude of said view vector; specifying a neighborhood of a viewing singularity; relating said view vector attitude to said neighborhood; and providing a certain image orientation whenever said view vector is within said neighborhood.

BRIEF DESCRIPTION OF THE DRAWINGS

FIG. 8 shows how the endoscopic information is displayed.

DETAILED DESCRIPTION OF THE INVENTION

Figure 1A:
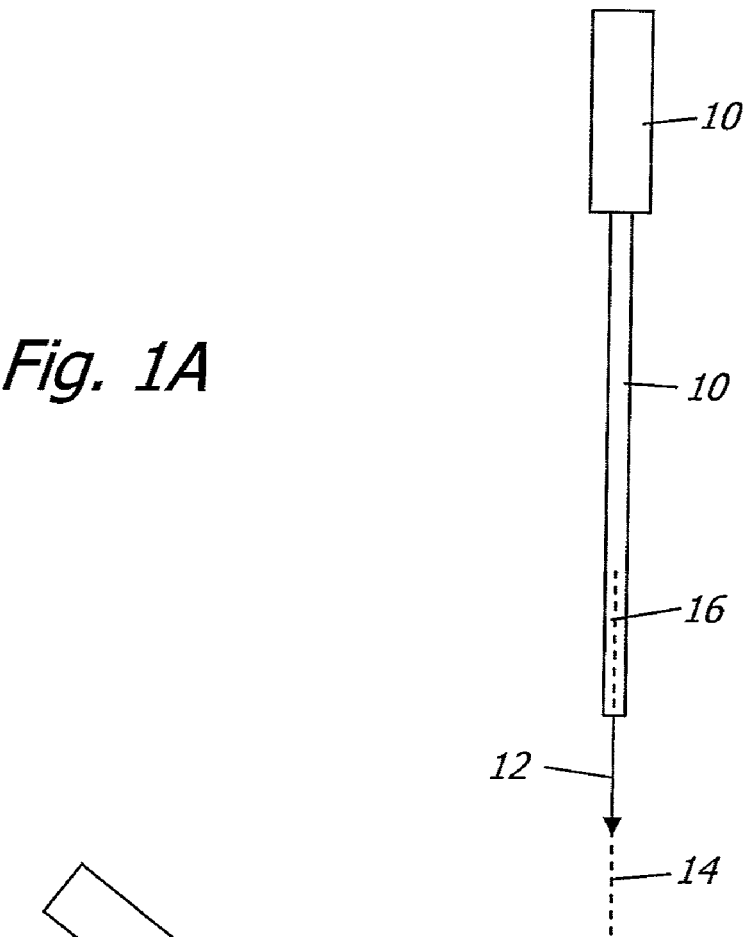
FIGS. 1A and 1B illustrate viewing singularities.
Figure 1B:
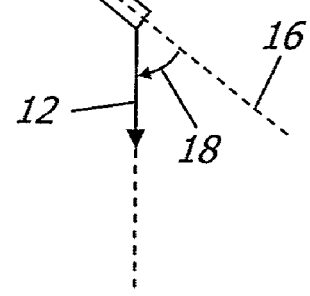

FIGS. 1A and 1B schematically show singular configurations for endoscopes 10 which include the sensing means required for leveling the endoscopic image. The sensing means could be housed anywhere in an endoscope depending on the type of scope; for a rigid endoscope it is typically more practical to put the sensing means in the proximal portion, while for flexible endoscopes it is generally necessary to put the sensing means near the tip. The endoscopic line of sight is represented by a view vector 12. When the view vector 12 is parallel to the direction of gravity 14, whether pointing up or down, it is in a singular configuration where the endoscopic image has no inherent up-direction. For rigid straight-viewing endoscopes where the view vector 12 is aligned with the longitudinal axis 16 of the endoscope 10, the singular configuration occurs when the endoscope 10 is vertical (FIG. 1A). For oblique viewing endoscopes the attitude of the endoscope 10 when in a singular configuration depends on the angular offset 18 between the scope longitudinal axis 16 and the view vector 12 (FIG. 1B). This is also true for flexible and rigid variable direction of view endoscopes which have a variable offset 18.

Figure 2A:
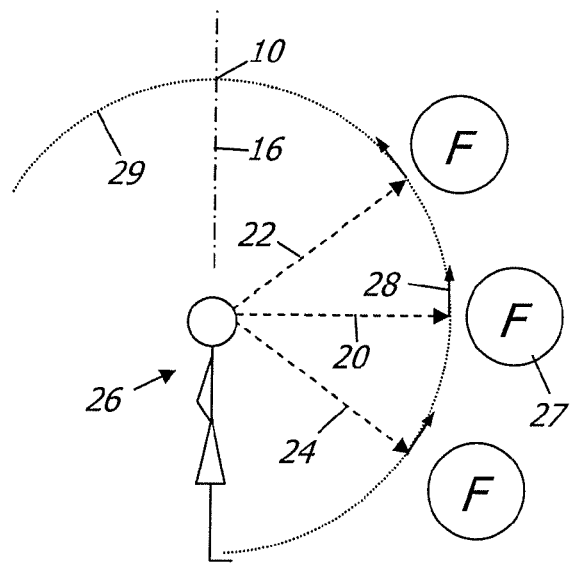
FIGS. 2A, 2B, 2C, and 2D illustrate the concept of singular viewing configurations as they relate to humans.
Figure 2B:
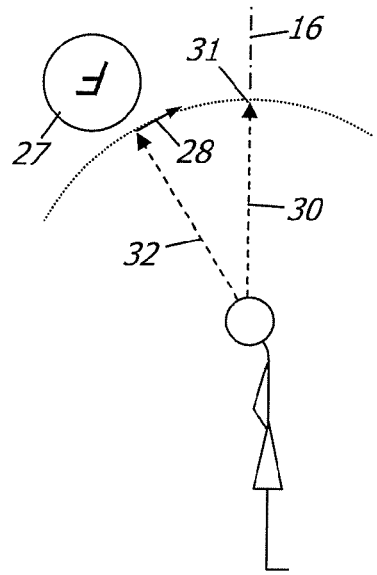
Figure 2C:
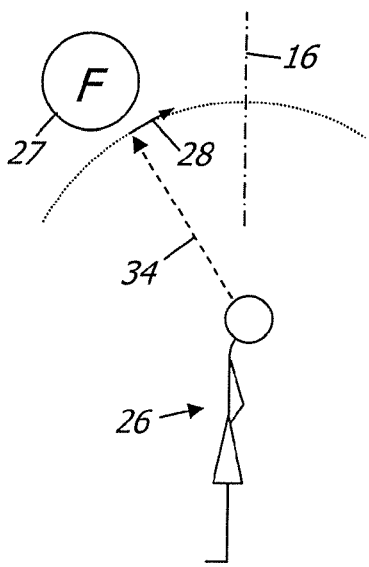
Figure 2D:
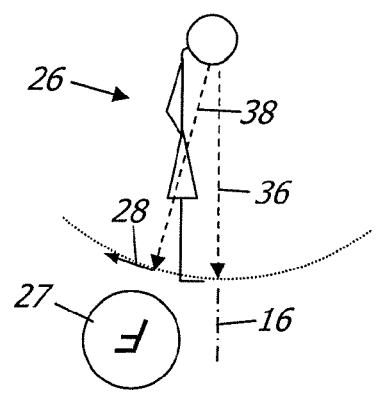

FIGS. 2A, 2B, 2C, and 2D illustrate the human viewing process in relation to the vertical orientation of our view field. When looking straight ahead 20 or slightly above 22 or below 24 an imagined equator (not shown) centered on a viewer's 26 head, the up-direction is obvious and the image 27 seen by the viewer 26 is correctly oriented (FIG. 2A). It is indicated by an up-vector 28 which is a projection of the gravity direction 16 onto the view field. The up-vector 28 is normal to the line of sight. As the viewer 26 tilts her head further upward along an imaginary arc 29, she finally reaches a configuration where her line of sight is parallel to the direction of gravity 16 and is looking straight up 30. In this configuration the up-vector is horizontal and there no longer exists an obvious up-direction. This is very much like standing at the North Pole and being asked to decide which way is south. A viewing pole 31 can be defined as the intersection between the arc 29 and the direction of gravity 16. As the viewer 26 tilts her head further she actually starts looking behind 32 herself and the image she now sees 27 is flipped both up to down and left to right (FIG. 2B) with the up-vector 28 having been reflected about the gravity axis 16. For a human the brain and equilibrium senses help with the interpretation of such a situation such that the viewer 26 is never confused as to her orientation in space. Our environment also gives us strong visual clues like vertical and horizontal lines to aid our orientational understanding. However, an endoscope does not provide information processing like the human brain, and a typical endoscopic environment does not have inherent directional clues. Thus, as an endoscopic view vector is swung past a pole (and into a different hemisphere), it is not clear how the image should be displayed. Displaying the endoscopic image reversed up to down and left to right is consistent with the human viewing configuration 32, but arguably the image should be displayed is if viewed from the configuration of FIG. 2C where instead of having tilted her head beyond the singular configuration 30, the viewer 26 has turned her entire body around and tilted her head up 34. A similar discussion is relevant when the viewer 26 swings her line of sight through the downward singular configuration 36 (FIG. 2D) to another backwards viewing configuration 38. The present invention lets the user interactively select how she would like the endoscopic counterpart to the image 27 displayed.

Figure 3A:
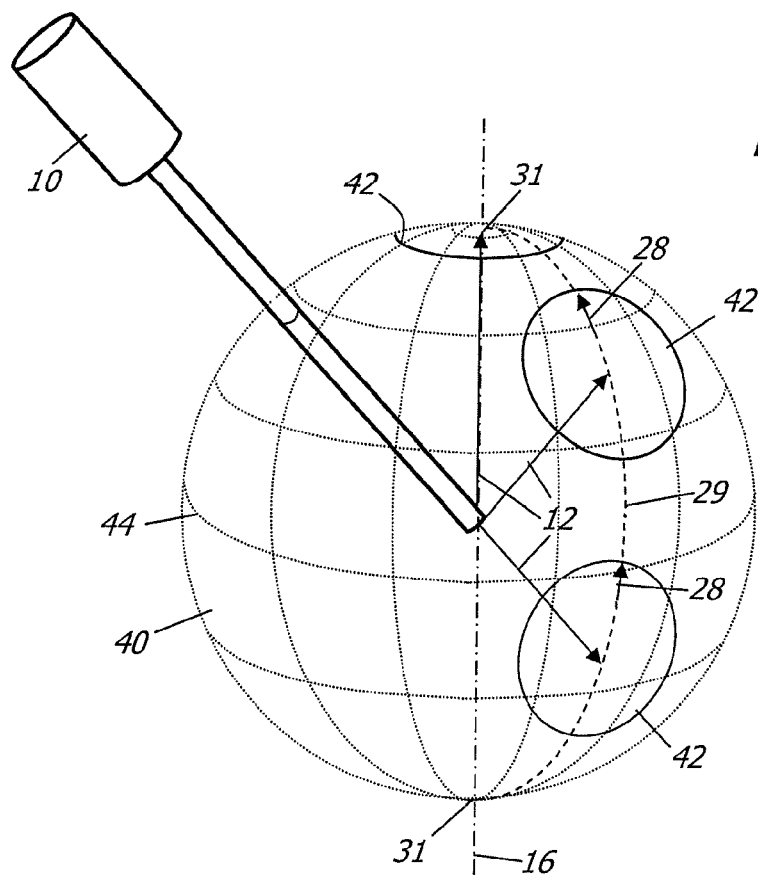
FIGS. 3A, 3B, 3C and 3D show a theoretical endoscopic viewing sphere and the issue of how to define the view-up vector in an endoscopic view.
Figure 3B:
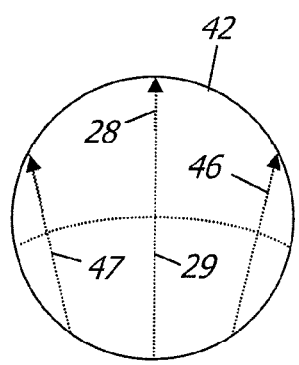
Figure 3C:
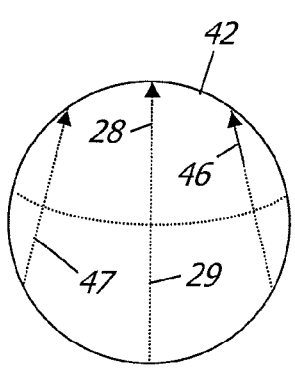
Figure 3D:
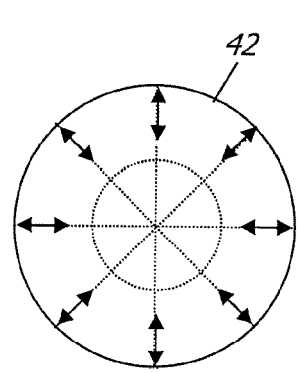

FIGS. 3A, 3B, 3C, and 3D illustrate these orientation issues further. A theoretical viewing sphere 40 (a three dimensional version of the viewing arc 29 in FIG. 2) is centered on the tip of an endoscope 10, as shown in FIG. 3A (The orientation of the endoscope 10 is not relevant). As the tip of the view vector 12 is moved along a longitudinal arc 29 the up-directions of points within the endoscopic view field 42 are continuously changing. When looking below the equator 44 lines of longitude 29, 46, 47 diverge (FIG. 3B), and when looking above the equator 44 lines of longitude 29, 46, 47 (FIG. 3C) converge. Thus, the up-direction 28 varies throughout the view field 42. The severity of this variation depends on the position of the view vector 12 in the viewing sphere 40 and the size of the view field 42. As the poles 31 are approached, this variation gets worse, and different points within a view field 42 can have diametrically opposite up-vectors. At the poles 31 there is mathematically no up-direction and in the neighborhood of the poles 31 the up-vector varies rapidly because the lines of longitude radially diverge or converge (FIG. 3D).

Figure 4:
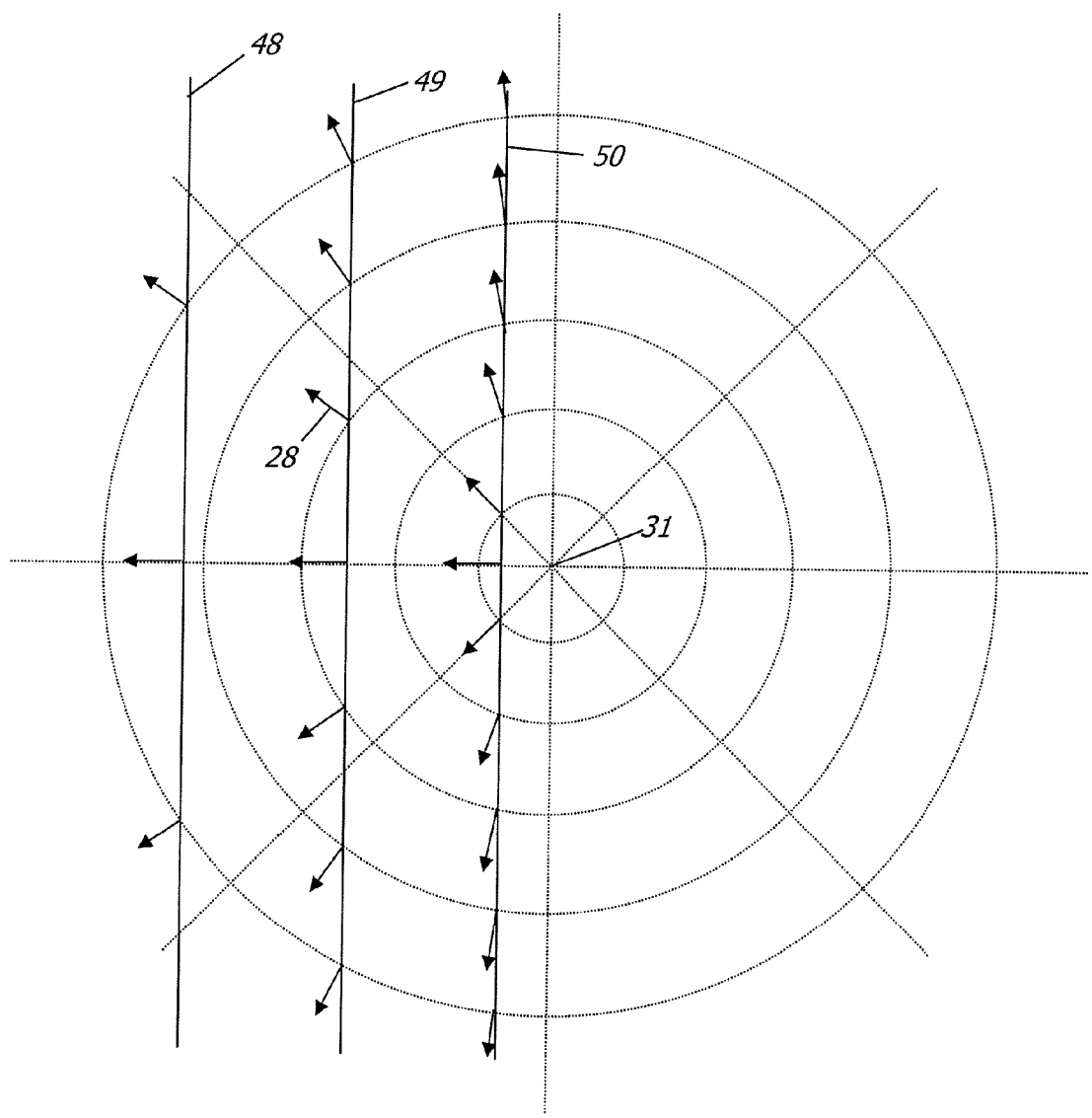
FIG. 4 shows view vector trajectories passing near a pole.

This rapid up-vector variation at the poles and in the neighborhood of the poles is what causes problems for the current gravity-leveled endoscopic systems. When the user manipulates the endoscope and moves the view vector in the vicinity of a pole 31, the image rotates rapidly. This is illustrated in FIG. 4, which shows a set of trajectories 48, 49, 50 swept out by the tip of the endoscopic view vector (not shown). The closer a trajectory is to the pole 31, the more severe the variation in the up-vector 28. Thus, near the pole 31 even small movements of the endoscope can cause a rapid image reversal. At the pole 31 itself the image will suddenly flip without warning. This problem is annoying to the surgeon even when using rigid straight viewing endoscopes where the user has a chance of predicting image rotations and flips based on the attitude of the endoscope. It is worse for oblique or variable direction endoscopes where the relationship between the endoscope axis and the hidden view vector direction is not obvious such that image reversals are unpredictable.

Figure 5:
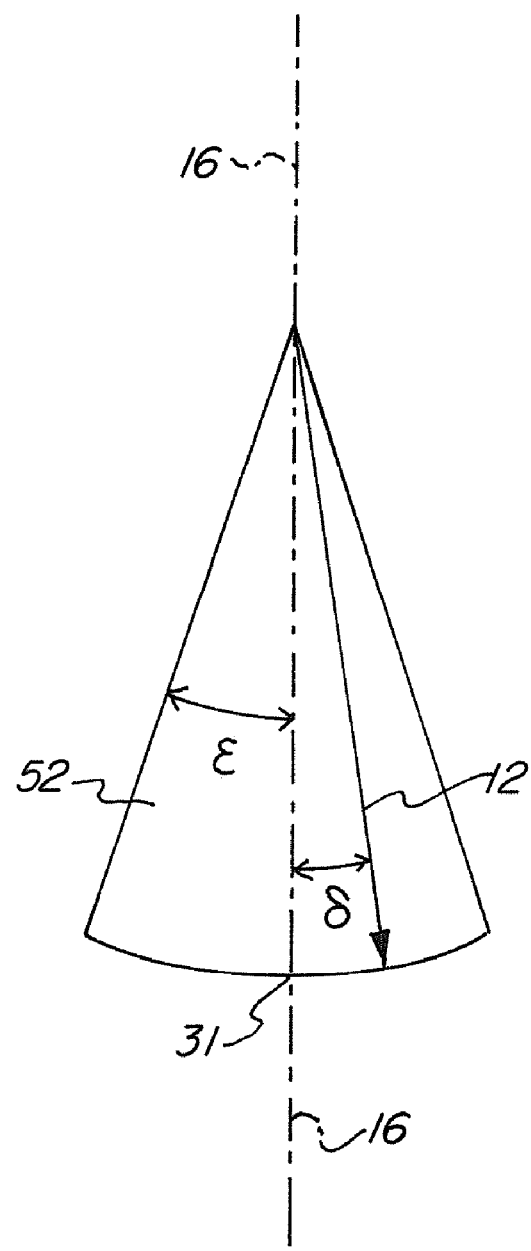
FIG. 5 shows a neighborhood around a pole.

These singularities are inherent to the physical universe and can not be removed. They can however be artificially masked or altered with mathematics and electronic processing. As shown in FIG. 5A, the most effective way to deal with the image spin is to mathematically define a neighborhood 52 around a singular configuration in which the image spin is reduced or eliminated by electronic processing. Using the mathematical framework disclosed in U.S. patent application Ser. No. 10/829,767 Schara et al., the angle that the view vector 12 makes with the direction of gravity 16, $\delta$, is given by equation 1:

$$\delta = \arctan\left[\frac{\cos\alpha\cos\phi - \sin\alpha\sin\phi\sin(\beta + \theta)}{\cos^2(\beta + \theta)\sin^2\alpha + (\cos\alpha\sin\phi + \cos\phi\sin\alpha\sin(\beta + \theta))^2}\right] \quad (1)$$

$$\delta \leq \varepsilon \quad (2)$$

Equation 2 defines a neighborhood 52 around a singularity. When the position of the endoscope is such that the view vector angle $\delta$ satisfies this equation, where $\varepsilon$ can be selected according to preference, the view vector 12 is said to be in the neighborhood 52 of a singularity. This neighborhood 52 can be thought of as a cone centered on the direction of gravity 16. Any time the view vector 12 falls within this cone 52, Equation 2 is satisfied (This applies to both the south and north poles. Depending on implementations and definitions, the neighborhood around the north pole could be defined with (180-$\varepsilon$) substituted for $\varepsilon$). Other definitions of a neighborhood of a singularity can also be used.

Figure 6A:
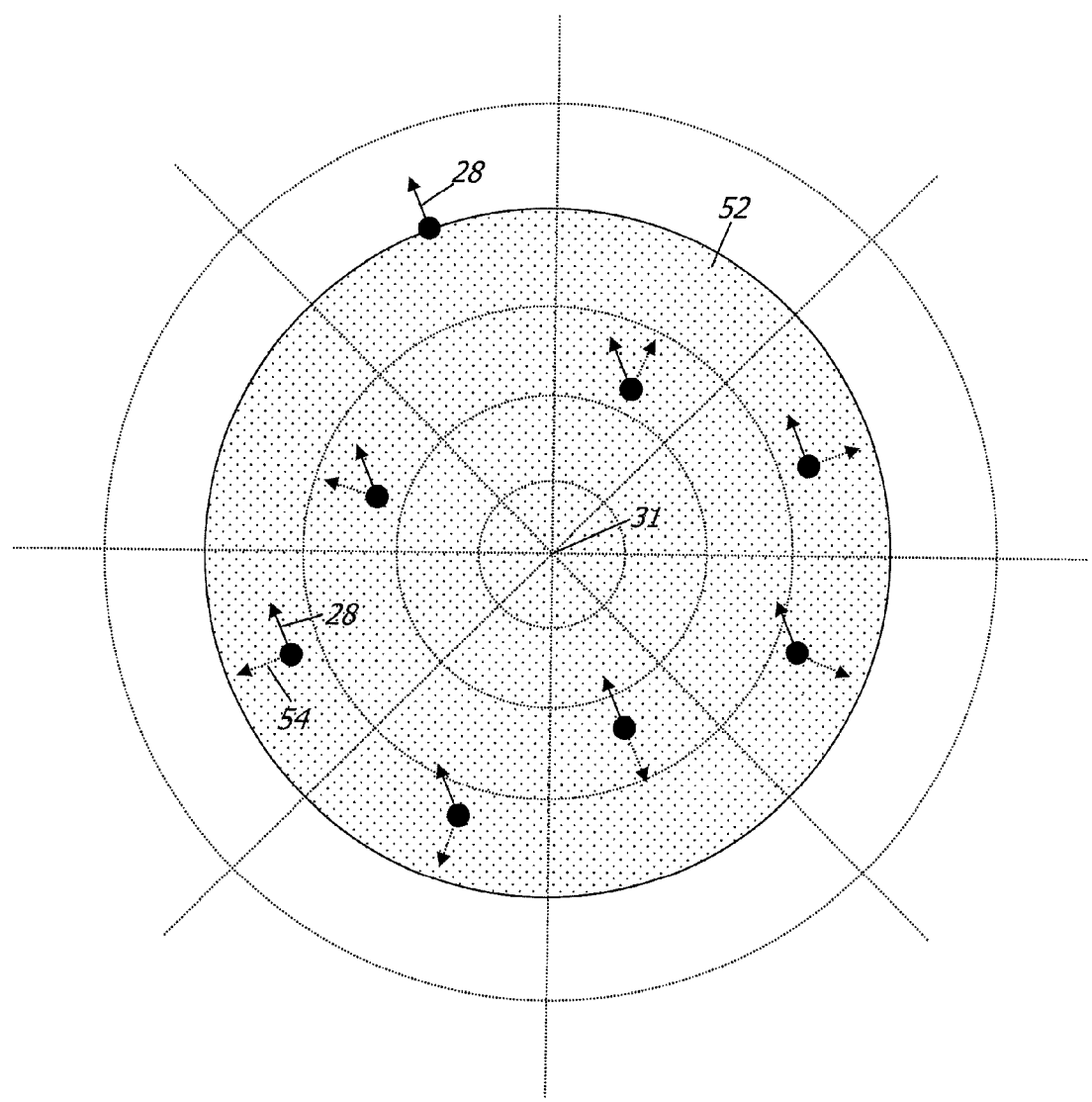
FIGS. 6A, 6B, 6C, and 6D show maintaining a specific up-vector within a neighborhood and the indication of a pole and the maintained up-vector as the endoscopic view swings towards a pole and through a pole to its other side.
Figure 6B:
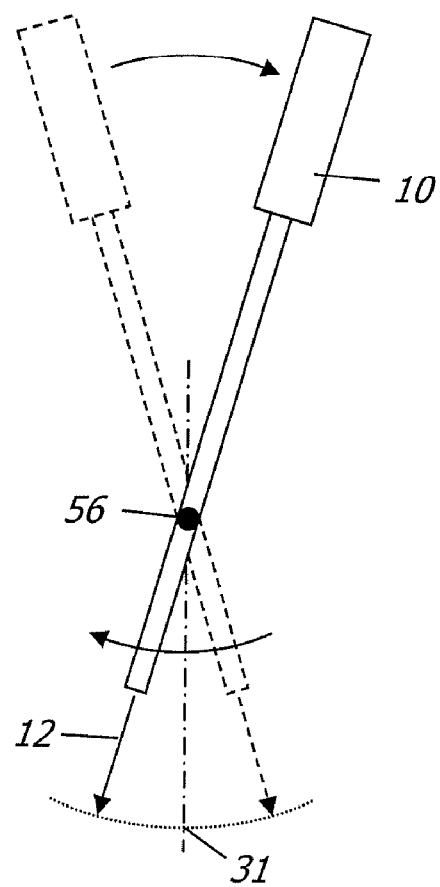
Figure 6C:
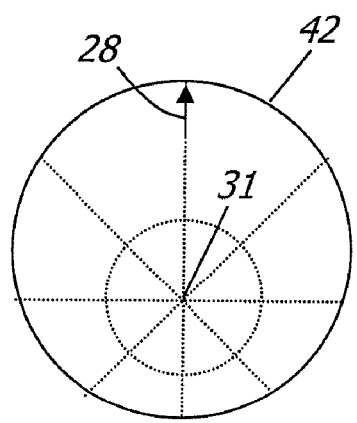
Figure 6D:
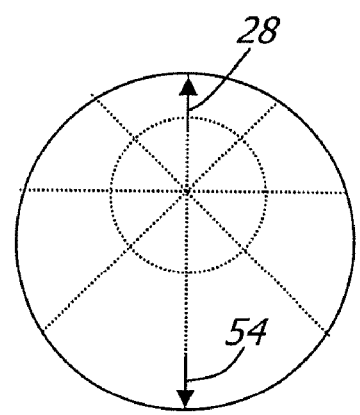

The attitude of the view vector is continuously monitored by the rotation pick-up sensors and a processor compares its configuration to the set of configurations contained within a neighborhood of a singularity. As shown in FIG. 6A, when the view vector is within the neighborhood 52, the user can either specify a desired image up-vector, or the processor can instruct the automatic leveling system to maintain the former up-vector 28 which existed when the view vector moved into the neighborhood 52. For a particular viewing position on the surface of the theoretical viewing sphere near the south pole 31 the endoscopic image would thus be kept in an artificially imposed orientation 28 instead of following the natural up-direction 54 which would exist at any point within the neighborhood 52 (It would be the same for the north pole except that the up-direction would be towards rather than away from the pole). For example, if a user pivots an endoscope 10 about its patient entry point 56 such that the view vector 12 and view 42 swing to the other side of the pole 31 (FIGS. 6B, 6C, 6D), it will often be desirable to maintain the up-direction 28 that existed before the pole 31 was traversed rather than using the theoretically correct up-direction 54 for the new viewing configuration. This scenario is analogous to the situation in FIG. 2D. When the viewer 26 looks down past her feet and behind herself, she may still be inclined to think of up as the direction in which her feet are pointing.

Figure 7A:
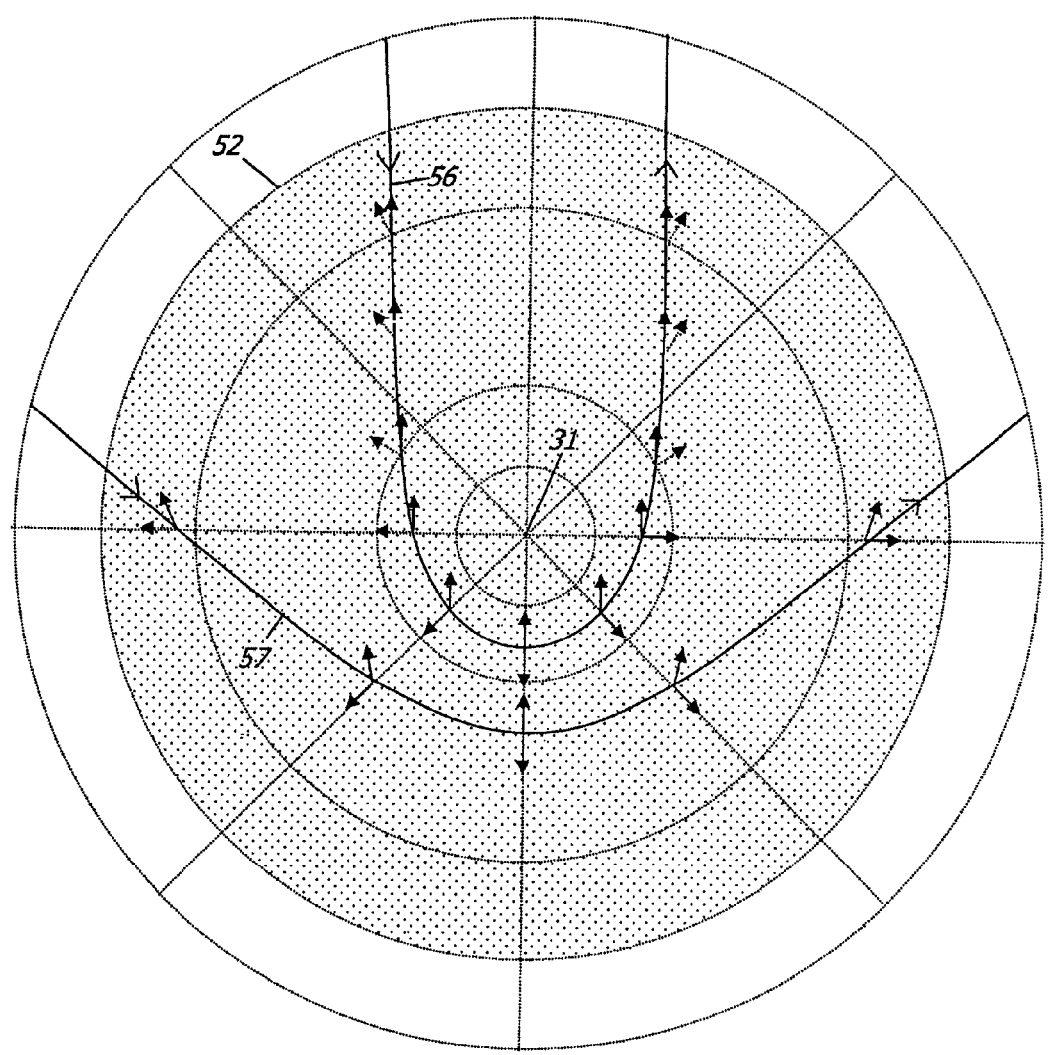
FIGS. 7A and 7B illustrate the concept of maintaining an image orientation as the endoscopic view swings through a pole and exits in a direction different from the entry direction.
Figure 7B:
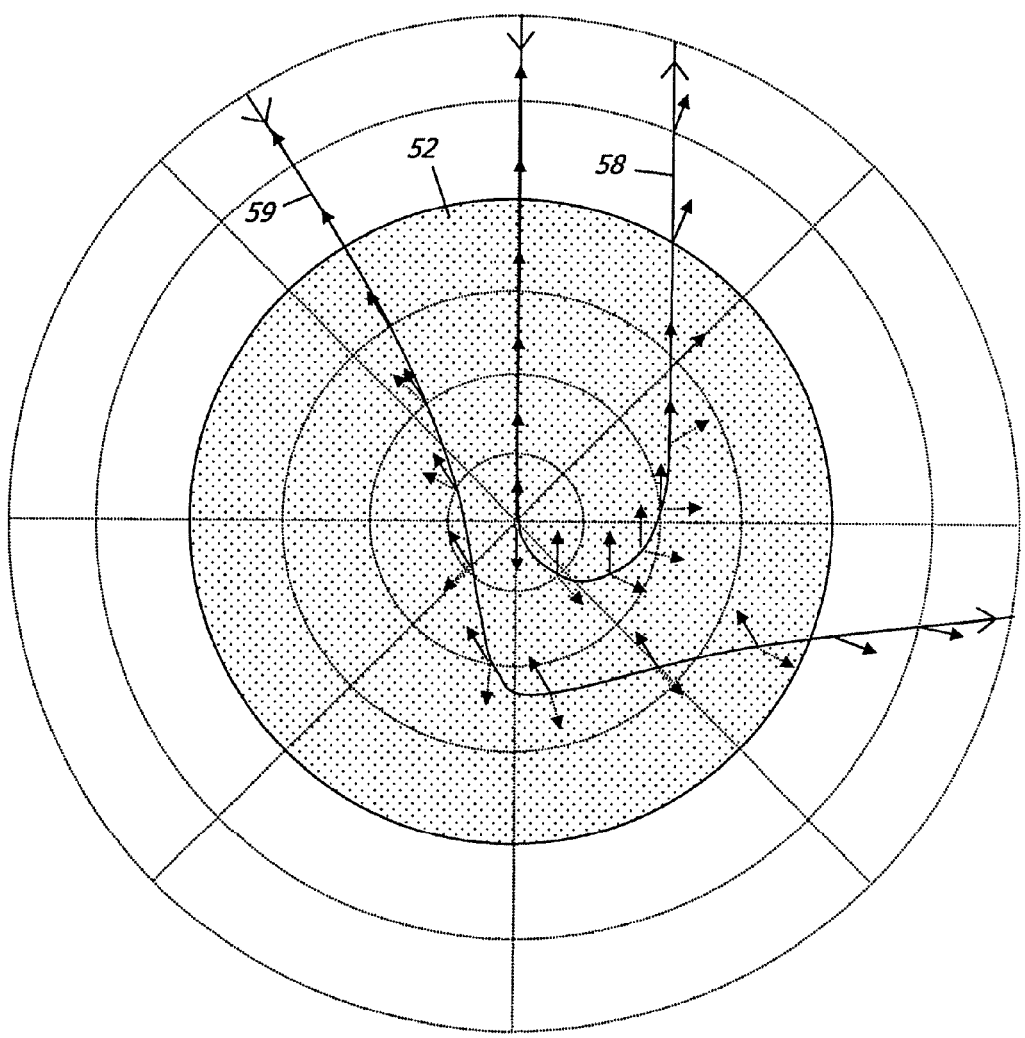
Figure 9:
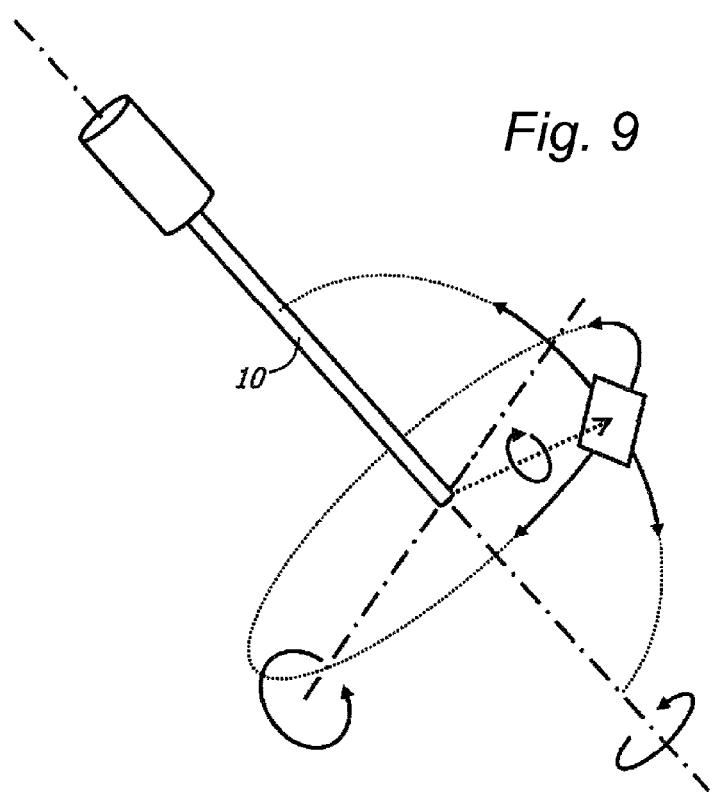
FIG. 9 illustrates movement of the endoscope in multiple degrees of freedom.

FIGS. 7A and 7B show the result of the present invention as the view vector enters a neighborhood 52 along some trajectory 56. The image leveling system maintains the up-direction which existed at the time the view vector crossed over the boundary of the neighborhood 52. Alternate view vector trajectories 57, 58, and 59 associated with various scope manipulations are shown in FIG. 7B. It should be noted that as the view vector leaves the neighborhood 52, the image will again be leveled according to the gravity leveling system, and for certain trajectories the image orientation may suddenly adjust itself a significant amount depending on the definition of the neighborhood 52. If the neighborhood 52 has a definite boundary, there will be a discontinuity at the boundary, but if it is defined with a soft boundary, the image orientation may follow a smooth and slow varying function, as in trajectory 57. In essence, what the neighborhood 52 does is artificially mask the singularity, and this mask can be defined by any appropriate mathematical function. For example, a neighborhood can be set up such that the endoscopic view is gravity leveled in certain regions and traditional in other regions. In addition to the size of a neighborhood, as specified by a relation such as Equation 2, the neighborhood can also have a directionality. The directionality of a neighborhood determines the endoscopic image orientation (and up-vector) when the view vector is within the neighborhood, and this directionality can be specified by a rule or a mathematical function. The neighborhood can be tailored according to the endoscopic procedure. For instance, if the user simply expects to generally swing the endoscope past a pole 31 and then back out in a direction generally parallel to the entry direction (trajectories 56, 58), then the neighborhood 52 could be small because the exit path is close to the entry path and thus will not cause a drastic change in image orientation as the view vector leaves the neighborhood 52. The neighborhood 52 can also be changed or disabled by the user. In this way the user can dynamically select how she wants to view the environment according to personal preference. This is important because different users have different ways of thinking about the endoscopic space (For example, when a scope is swung back towards the user (FIG. 4A) some users may think of this as looking down and backwards, while others may think of this as standing on the other side and looking down and forwards.)

FIG. 8 shows a display 62, with an endoscopic image 64 of a certain anatomical feature 66. The boundary of a neighborhood is indicated by a line of latitude 68. An indicator of the image center 70 can be selectively enabled to provide information about the relative location of a pole, indicated by a dot 72. The display 62 includes a graphical model 74 of the global viewing configuration, including graphical models of the endoscope 76, view vector 78, gravity direction 80, singularity neighborhood boundary 82, and viewing sphere 84. These graphical models aid the viewing process by providing the user with information about the relative arrangement of the view vector and the singular configuration. Buttons 88 are provided for the user to interactively manage image orientation and neighborhood settings. For example, the user may select to toggle the image orientation between the current upright image orientation maintained within a neighborhood and the natural upright orientation which would exist without the neighborhood setting. Also, the user can select to display the pole and alternately a full coordinate grid. The interface also features an optional warning flag 90 which shows up when the endoscopic view vector is in the vicinity a pole.

Methods for leveling the endoscopic image are described in the above disclosures, but the details of these methods are not necessary for an understanding of this invention.

The present invention has been described above in terms of a presently preferred embodiment so that an understanding of the present invention can be conveyed. However, there are many alternative arrangements for a method for providing gravity referenced endoscopic imaging not specifically described herein but for which the present invention is applicable. For example, an alternative mathematical framework describing the endoscope and its configurations would lead to an alternative formula for the view vector orientation and the neighborhood around a singularity. Also, there are many different ways to display the imaging information. In addition, while the examples were given with respect to endoscopes for use in surgical procedures, the present invention is equally applicable with respect to borescopes or the like for use within various mechanical structures. Therefore, the term "endoscope" as used herein, refers to an endoscope or any similar device such as a borescope, a fiberscope, etc.

This invention is not to be limited by the embodiments shown in the drawings and described in the description, which are given by way of example and not of limitation, but only in accordance with the scope of the appended claims.

We claim:

1. A method for avoiding rapid or sudden image rotation in a gravity leveled endoscopic imaging system, comprising:
   receiving an input specifying a neighborhood size and directionality from a user;
   monitoring the attitude of said view vector wherein said monitoring comprises accounting for endoscope pitch, endoscope roll, and view vector angle relative to the endoscope axis;
   specifying a neighborhood of a viewing singularity based on said user input;
   repeatedly comparing said view vector attitude to said neighborhood wherein said comparing comprises determining whether said view vector is within said neighborhood; and
   providing a certain image orientation according to said neighborhood directionality whenever said view vector is within said neighborhood;
   wherein said certain image orientation is based on an image up vector specified by the user.

2. The method of claim 1, wherein said certain image orientation is the image orientation which existed as said view vector entered into said neighborhood.

3. The method of claim 1, wherein said directionality of said neighborhood comprises a smooth mathematical function.

4. The method of claim 1, further comprising indicating to the user whenever said view vector enters said neighborhood.

5. The method of claim 1, wherein the input specifying a neighborhood size and directionality is received from a user via a graphical user interface.

6. The method of claim 1, wherein the input specifying a neighborhood size and directionality is received from a user via a graphical user interface.

7. A method for avoiding rapid or sudden image rotation in a gravity leveled endoscopic imaging system, comprising:
receiving an input specifying a neighborhood size and directionality from a user;
monitoring the attitude of said view vector wherein said monitoring comprises accounting for endoscope pitch, endoscope roll, and view vector angle relative to the endoscope axis;
specifying a neighborhood of a viewing singularity based on said user input;
repeatedly comparing said view vector attitude to said neighborhood wherein said comparing comprises determining whether said view vector is within said neighborhood; and
providing a certain image orientation according to said neighborhood directionality whenever said view vector is within said neighborhood;
wherein the input specifying a neighborhood size and directionality is received from a user via a graphical user interface.

8. The method of claim 7, wherein said certain image orientation is the image orientation which existed as said view vector entered into said neighborhood.

9. The method of claim 8, wherein said image orientation is based on an image up vector that existed when the view vector moved into the neighborhood.

10. The method of claim 7, wherein said directionality of said neighborhood comprises a smooth mathematical function.

11. The method of claim 7, further comprising indicating to the user whenever said view vector enters said neighborhood.

12. A method for avoiding rapid or sudden image rotation in a gravity leveled endoscopic imaging system, comprising:
receiving an input during a medical procedure from a user manipulating an endoscope during the medical procedure that specifies a neighborhood size and directionality from the user;
monitoring the attitude of said view vector wherein said monitoring comprises accounting for endoscope pitch, endoscope roll, and view vector angle relative to the endoscope axis;
specifying a neighborhood of a viewing singularity based on said user input;
repeatedly comparing said view vector attitude to said neighborhood wherein said comparing comprises determining whether said view vector is within said neighborhood; and
providing a certain image orientation according to said neighborhood directionality whenever said view vector is within said neighborhood.

13. The method of claim 12, wherein said certain image orientation is the image orientation which existed as said view vector entered into said neighborhood.

14. The method of claim 12, wherein said directionality of said neighborhood comprises a smooth mathematical function.

15. The method of claim 12, further comprising indicating to the user whenever said view vector enters said neighborhood.

16. The method of claim 12, wherein said certain image orientation is based on an image up vector specified by the user.

* * * * *